United States Patent [19]
Lübbers et al.

[11] Patent Number: 4,701,697
[45] Date of Patent: Oct. 20, 1987

[54] ARRANGEMENT FOR MEASURING POTENTIAL DIFFERENCES

[75] Inventors: Dietrich W. Lübbers, Dortmund; Norbert Opitz, Schwerte, both of Fed. Rep. of Germany

[73] Assignee: Max Planck Gesellschaft, Goettingen, Fed. Rep. of Germany

[21] Appl. No.: 572,927

[22] Filed: Jan. 20, 1984

[30] Foreign Application Priority Data

Jan. 21, 1983 [DE] Fed. Rep. of Germany ....... 3301939

[51] Int. Cl.$^4$ ............................................. G01N 27/00
[52] U.S. Cl. ...................................... 324/96; 324/453
[58] Field of Search ................... 324/96, 453, 72, 76 R

[56] References Cited

U.S. PATENT DOCUMENTS

4,344,035 10/1982 Conti et al. .......................... 324/453
4,510,441 4/1985 Yasuda et al. ........................ 324/96

OTHER PUBLICATIONS

Kuhn, Physical Methods of Chemistry, vol. 1, Wiley, New York, 1972, pp. 594–595, 600–601, 614–615, 618–619, 624–625, 680–681.

*Primary Examiner*—Ernest F. Karlsen
*Attorney, Agent, or Firm*—Michael J. Striker

[57] ABSTRACT

To measure potential differences in second-class conductors without interference potentials, there are provided a potential generator cooperating with a potential-measuring structure. This structure includes a substrate of electrically highly insulating and chemically inert material embedding optical indicators whose optical properties change as a function of the applied electric potential difference. Both the potential generator and the potential-measuring structure have boundary surfaces which are in contact with the second-class conductor and opposite surfaces interconnected by an equalizing conductor. A light-measuring device is arranged for intercepting light changes in the indicators, thus measuring the potential difference.

63 Claims, 25 Drawing Figures

ARRANGEMENT FOR MEASURING POTENTIAL DIFFERENCES

BACKGROUND OF THE INVENTION

The present invention relates in general to an arrangement for measuring differences of electrical potentials, and in particular to measuring potential differences in second-class conductors, such as ionized liquids.

In boundary layers or interfaces between solid bodies such as metals, ion-selective glasses, membranes and also liquids on the one hand, and ion-containing liquids generally called second-class conductors on the other hand, potential differences frequently occur, and the measurement of such differences is of particular interest. Interfaces of this kind in the following description will be referred to as potential-generating layers.

For example, known are ion-selective electrodes provided with membranes of synthetic material acting as potential-generating layers (Cammann "Das Arbeiten mit ionenselektiven Elektroden", Springer, Berlin, 1973), with which, upon immersion in an ion-containing solution, potential differences occur which correspond to the activity of ions under measurement. In this manner a large number of ions can be determined.

Such known electric measuring means employed for measuring the potential difference cause however a serious problem, inasmuch as the metals which connect amplifying or indicating devices to respective measuring electrodes, when immersed in the ion-containing solutions, produce themselves potential differences, and a chain of potentials will result due to which an unambiguous correlation between the measured potential difference and that of the potential generator itself, or the calculation of the resulting interfering potentials, is not always possible. This problem represents a particularly disturbing limitation of the measuring accuracy, because the interfering potentials always depend on the particular substance under measurement, and for example in biological measuring substances they can hardly be predetermined as far as their magnitude and time behavior are concerned.

For instance, the drift and the absolute value of potential differences cannot be determined in advance in many cases when calomel electrodes or also Ag/AgCl electrodes are used in biological objects.

In the application of liquid compounds between the indicating device and the measuring probe, applied for example by means of agar pipettes, frits or capillaries, does not result in any satisfactory solution of the problem, because such solutions in most cases become quickly contaminated, produce parasitic diffusion potentials, or contaminate the measured substance.

SUMMARY OF THE INVENTION

It is therefore a general object of the present invention to overcome the aforementioned disadvantages.

More particularly, it is an object of the invention to provide an improved arrangement for measuring potential differences, in which the influence of interfering potentials which affect the measurement of potentials in second-class conductors is substantially reduced.

In keeping with this object and others which will become apparent hereafter, one feature of the invention resides, in a combination which comprises a potential generator which produces the potential difference to be measured, a potential-measuring structure of electrically highly insulating and chemically inert material which includes an electrooptic indicator which reacts to a change in the electric potential difference by changing its optical quality, the potential generator and the potential-measuring structure including respectively an interface in contact with the second-class conductor (measured object), an equalizing conductor connecting the potential generator and the potential-measuring structure, and a light-measuring device coupled to the electrooptical indicator for measuring the change of its optical quality.

The arrangement according to this invention has the advantage that potential differences occurring at the potential generator can be measured without any reactive effect because the potential-measuring structure does not react chemically with the measuring object, and the generation of an optical signal such as a change in color, a secondary light emission such as for example luminescence, and particularly fluorescence, or other optical changes, do not produce any change in the exeunt potential difference as is the case in conventional potential-measuring methods using reference electrodes.

According to another feature of this invention, increased signals are produced in such a manner that the potential-measuring structure is in the form of a very thin film, so that high field strengths are present in the potential-measuring structure. Preferably, the film is made as a monomolecular layer.

Such monomolecular layers as well as films made of several molecular layers with a definite layer thickness can be produced according to known methods, described for example in Kuhn, Physical Methods of Chemistry, Volume 1, Wiley, New York, 1972.

If desired, the monomolecular layers can be doped with indicators or completely constructed of the indicators, and the intermediate layers may be made free of indicators.

The employed indicators can be polarized in a preferred direction or can be arranged in a flat or also a spatial array. In manufacturing such arrays, there can be employed different indicators in combination with each other, inasmuch as different and equally good preparations are possible when for example, instead of very thin films, natural or synthetic membranes such as phospholipid membranes or indicator-doped boundary layers between two second-class conductors are used.

The arrangement according to this invention has a particularly low susceptibility to interferences when the potential generator is situated in close proximity to the potential-measuring structure. In this manner, exongenous interferences of the electric field are easily avoided.

Small-size arrangements according to this invention can be obtained when the potential-measuring structure and the potential generator are arranged in a sandwich-like fashion and the equalizing conductor is in the form of an intermediate layer, or when the potential generator and the potential-measuring structure are arranged concentrically with one another and the potential-measuring structure is optically coupled to a light conductor.

Further increase of signal is obtained when the potential-measuring structures or their immediate environment are provided with means for concentration of the electric field.

An improved adjustment to different kinds of measuring objects, and simultaneously an enlargement of the measuring surface, can be achieved when the potential-measuring surfaces and the potential generators have a mosaic-like structure.

In order to pick up optically the measuring object and the potential-measuring structure, there can be provided layers which produce absorption, reflection or dispersion or change the reflection index, the degree of polarization or the phase of the measuring light. Due to this optical decoupling, the optical reaction from the measuring object is reduced.

By providing the potential-measuring structure with electrically conductive layers which are light-permeable at least in the direction to the light-measuring device, it is possible to apply in situ a biasing voltage or a calibration voltage to the potential-measuring structure, and hence to calibrate the entire measuring arrangement.

In order to integrate the potential generator with the potential measuring structure, the latter is made in the form of a highly insulating membrane in which microscopic potential generators are arranged. These micropotential generators are ion channels in the form of mechanical pores, doped transport molecules (carrier dopings), metallic particles or particles of ion-selective glass.

From the standpoint of measuring technology, fluorescent indicators are particularly advantageous, because of their satisfactory signal-noise ratio. A particularly advantageous indicator of this kind is 3,3'-dipropylthiadicarbocyanine-iodide.

The novel features which are considered characteristic for the invention are set forth in particular in the appended claims. The invention itself, both to its construction and its method of operation, together with additional objects and advantages thereof, will be best understood from the following description of specific embodimetns when read in connection with the accompanying drawing.

BRIEF DESCRIPTION OF THE DRAWING

FIGS. 2a–2m show different arrangements for enhancing the field strength in the arrangement of this invention;

DESCRIPTION OF THE PREFERRED EMBODIMENTS

Figure 1A:
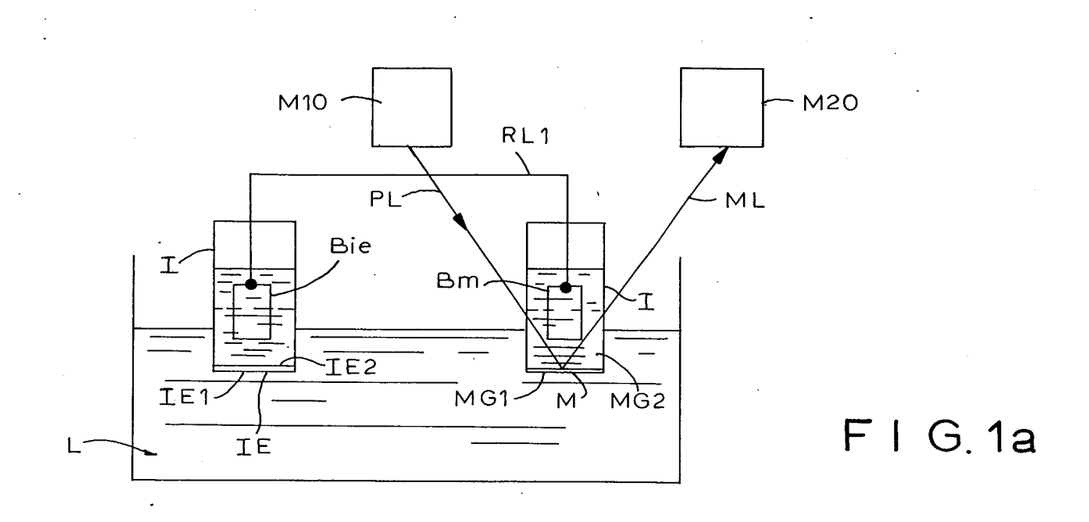
FIGS. 1a–1d illustrate schematically different embodiments of the measuring arrangement of this invention.

Referring firstly to FIG. 1a, there is illustrated an ion-containing solution L (second-class conductor) and a boundary layer or interface IE (potential generator) defining a surface IE1 in contact with the solution L and an opposite surface IE2 which is surrounded by an envelope I of electrically insulating material. According to the Nernst equation there results a potential $$E_i = E_i^o + \frac{RT}{Z_iF} \ln A_i \qquad (1)$$

wherein
$A_i$ denotes the activity of the measured type of ions;
$Z_i$ is the valence of the measured type of ions;
F is the Faraday constant;
R is the gas constant;
T is the temperature in degrees Kelvin; and
$E_i^o$ is the standard potential.

The potential $E_i$ is applied via a first reference electrode $B_{ie}$ and an equalizing metallic conduit RL1 to a second reference electrode $B_m$ which establishes the connection with a potential-measuring structure M. The potential-measuring structure M is made of a highly insulating and chemically inert material and defines opposite boundary layers or interfaces MG1 and MG2. The two reference electrodes $B_{ie}$ and $B_m$ are immersed in the second-class conductor contained in respective envelopes I. Due to this arrangement, an equal potential is obtained, both at the sides IE2, MG2 turned away from the measuring object L and on the sides IE1, MG1 in contact with the measured solution L of the potential generator IE and of the potential-measuring structure M. In this manner, an equal potential difference is produced across the potential generator IE and across the potential-measuring structure M.

The potential-measuring structure M includes an optical indicator which changes its optical property proportionally with the change of the potential difference across the potential-measuring structure. These variable optical properties are its luminescence, particularly fluorescence, light absorption, light dispersion, its index of refraction, its behavior in changing phase of the light, or its degree of polarization. When the potential-measuring structure is illuminated by a testing light beam PL transmitted from a light source M10 and the reflected light beam ML is measured in a light-measuring device M20, then the change of the optical quality of the indicator is determined, and accordingly the corresponding potential difference is measured.

The light source M10 for the testing light beam can be any suitable device known in the art which emits light in a wavelength range which is adjusted to the employed indicator. Preferably, the light source M10 is in the form of a monochromator or polychromator provided with filters or dispersion elements. Also of advantage may be a laser beam source because of its superior capability of forming pulses and its possibility to form sharper bundles. Applicable are also light-emitting diodes which have the advantage of small size and low heat dissipation.

For transmitting the light beam, there can be used suitable lens or mirror arrangements or light conduits.

The light-measuring device M20 includes suitable photosensors known in the art, such as for example photomultipliers, photocells, photodiodes, and the like. For measuring local distribution of potentials, arrays of photocells of vidicons can be employed.

Figure 1B:
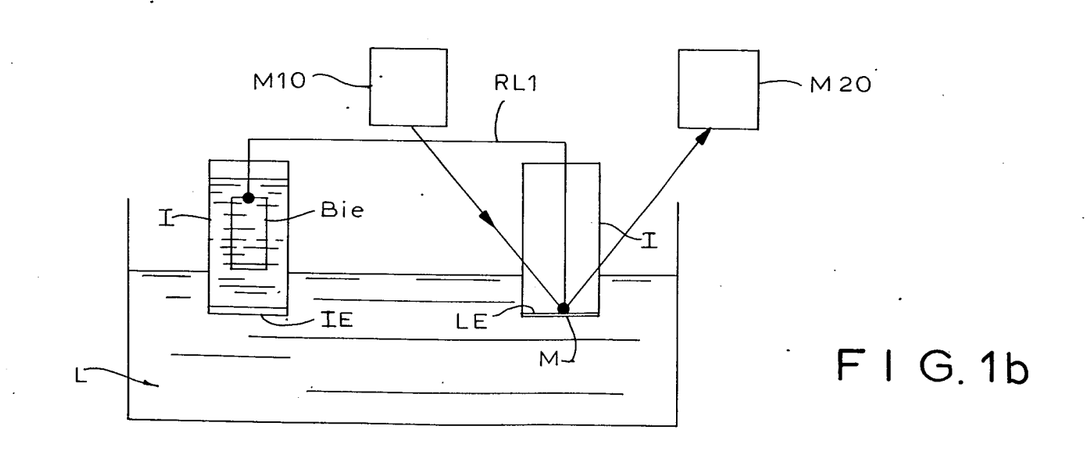
Figure 1C:
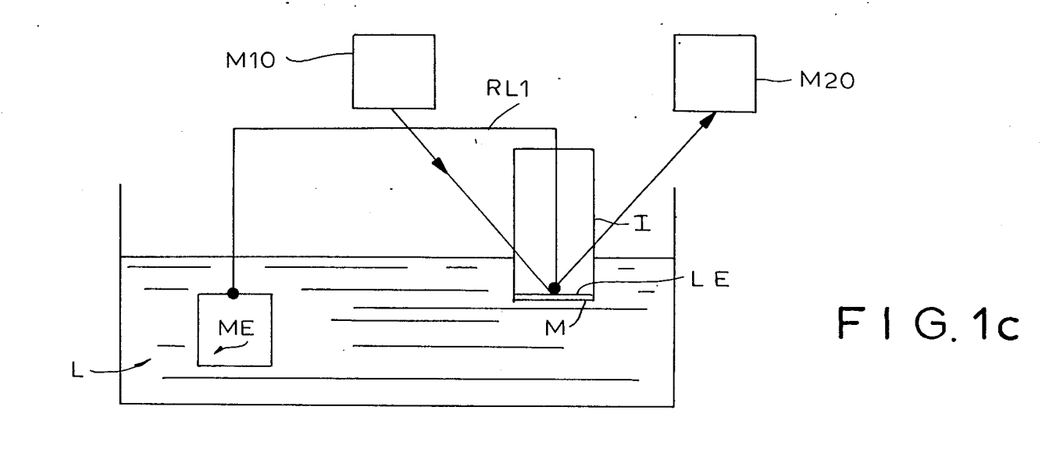

In a modification of the arrangement for measuring potential differences as shown in FIG. 1b, a potential-measuring structure M has its side remote from the measured solution L provided with a conductive electrode LE made of metal and connected with the equalizing conduit RL1. In this case the reference electrode $B_m$ which may act as a source of interference is eliminated. The second reference electrode $B_{ie}$ can also be eliminated when the potential difference is produced directly on a metal piece ME which is directly connected via a metal equalizing conduit RL1 to the conductive electrode LE on the potential-measuring structure M (FIG. 1c).

Figure 1D:
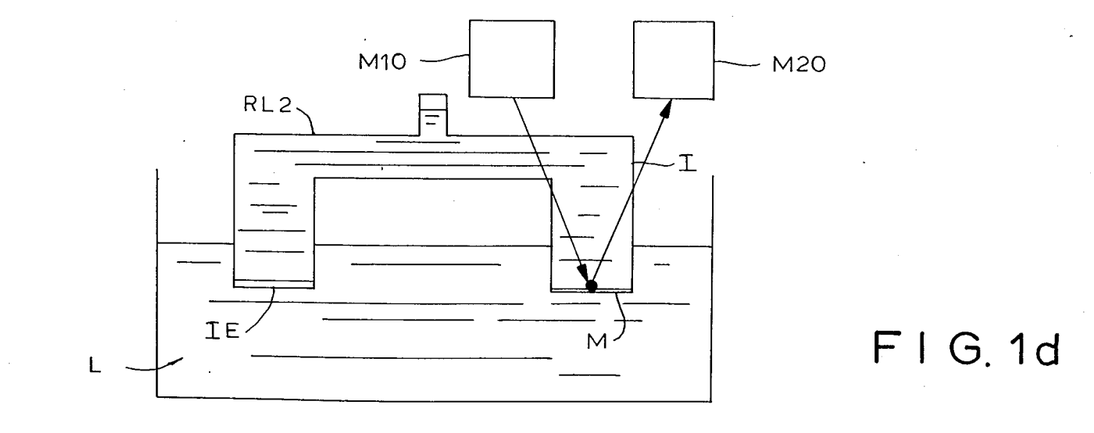

In another variation of the measuring arrangement according to this invention illustrated in FIG. 1d, a second-class conductor is used as the equlizing conductor RL2 between the potential generator IE and the potential-measuring structure M.

In a further elaboration of potential generators according to this invention, there are employed ion-selective electrodes. Such electrodes which can be constructed for use with a large variety of ions produce potential differences amounting to several millivolts across membranes having the thickness of the order of several microns. Provided that the potential-measuring structure M has a thickness in the range of several nanometers and is provided with indicators made for example of styryl coloring substances or of merocyanines, then depending on the applied electric field between the boundary surfaces MG1, MG2 of the potential-measuring structure M, field strengths of about $10^6$ Volt/cm are produced, which effectively change the fluorescence of such indicators and enhance the measurability.

Potential-measuring structures M of the requisite thickness can be manufactured in the form of membranes made of synthetic or natural materials doped with indicators. For example, there can be used phospholipid membranes as boundary layers, as monomolecular layers or composite structures made by conventional preparation methods of monomolecular multiple layers. These layers can be either doped with indicators or can be free of indicators or composed completely of indicator molecules. The indicators are filled in the layers, namely by a leakage-free covalent binding or by embedding in the membrane material. The employed membranes must have a low permeability for substances to be warded off, such as acids, which may cause extinction of fluorescence of the indicators. This quality is possessed by membranes made of polystyrene, for example.

Figure 2A:
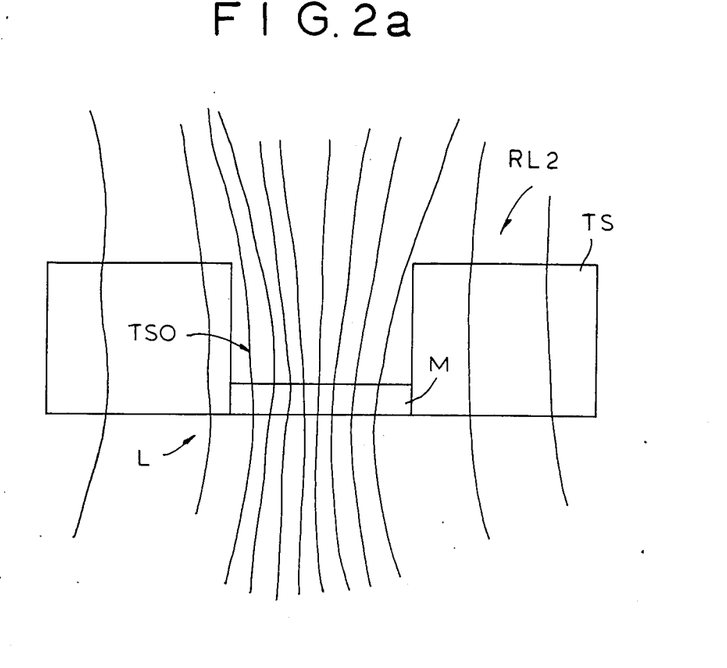

In the membranes, it is also possible to use means influencing electrical fields. According to FIG. 2a, which illustrates on an enlarged scale a part of the potential-measuring structure M in FIG. 1d, the density of electric field is increased by using an insulating supporting layer TS formed with an opening TS0 for the liquid equalizing conduit RL2. In this manner the field strength in the potential-measuring structure M is increased.

Figure 2B:
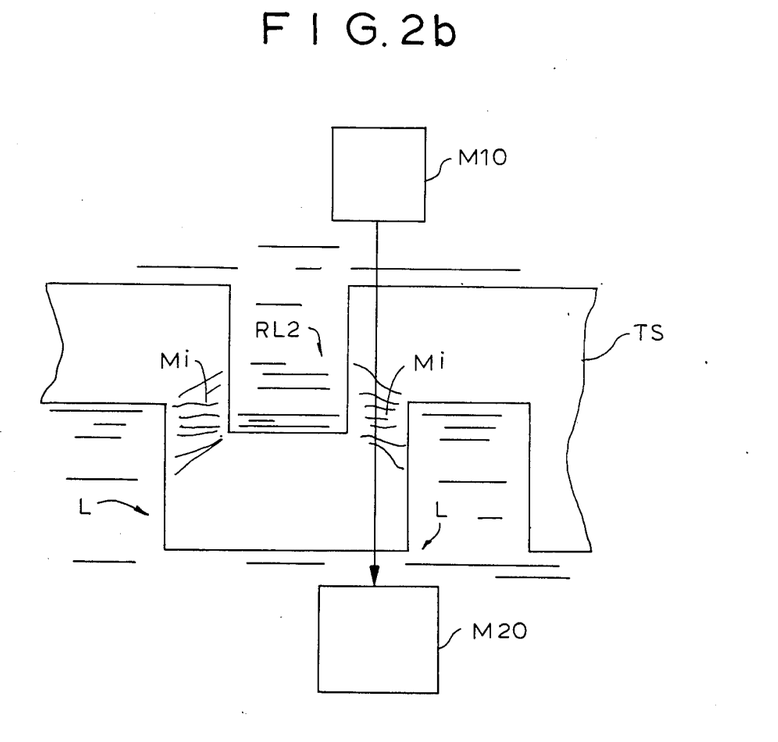

In the embodiment according to FIG. 2b, the electrical field lines of increased density are formed in the region having the shortest distance between the measured solution L and the liquid equalizing conduit RL2 (corresponding to MG1−MG2). In this embodiment, the potential-measuring structures $M_i$ are parts of the supporting layer TS. In the arrangement of FIG. 2b, the changes of the optical quality of the indicators embedded in the layer TS are measured directly by a through-going light beam.

Figure 2C:
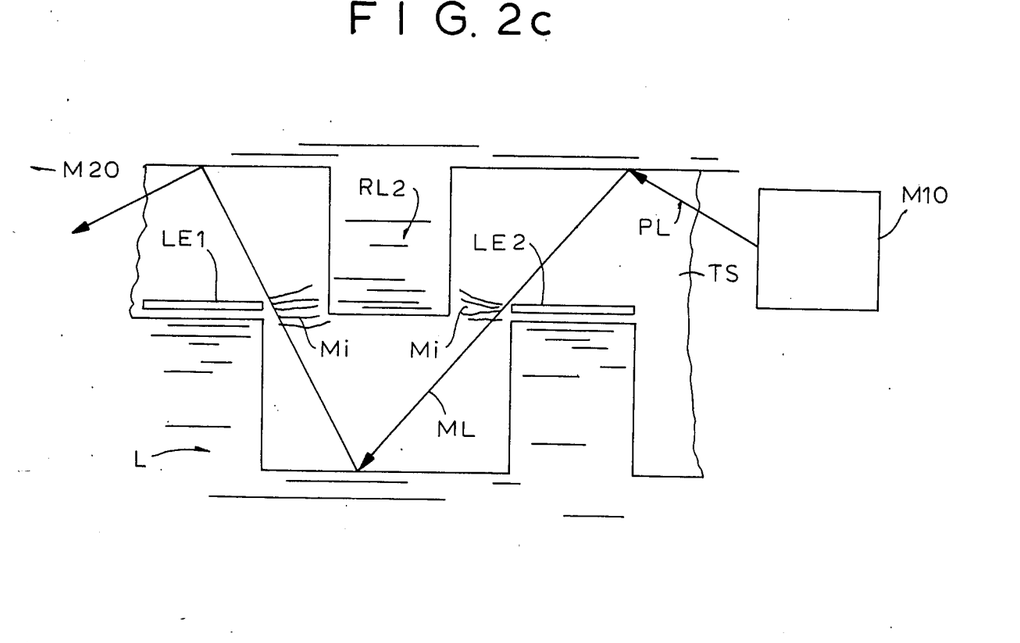
Figure 2D:
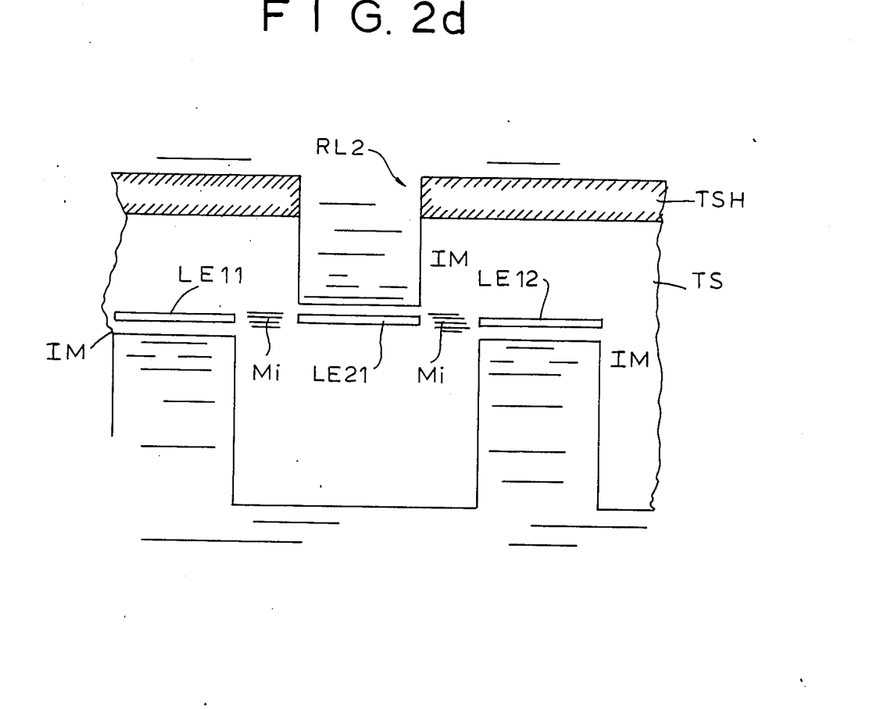

According to the embodiments of this invention illustrated in FIGS. 2c and 2d, the electric field is increased by using conductive electrodes $LE_i$, $LE_{ik}$ (reference characters $LE1_k$ denote the boundary surfaces MG1, and reference character $LE2_k$ denotes the boundary surfaces MG2). According to FIG. 2d, there is provided an additional supporting layer TSH of a high mechanical strength in order to reinforce the supporting layer TS. In order to facilitate manufacturing of the device of FIG. 2d, insulating layers IM are applied against the conductive electrodes from the outside.

In the arrangements where the supporting layers TS and the measuring structures $M_i$ are produced as a single piece, the testing light beam can be transmitted through a lateral side of the supporting layer, so that the latter acts as a light conduit (FIG. 2c). In this case, the supporting layer TS is made of a transparent material. The boundary surfaces of the supporting layer can be provided with a light-reflecting film.

Figure 2E:
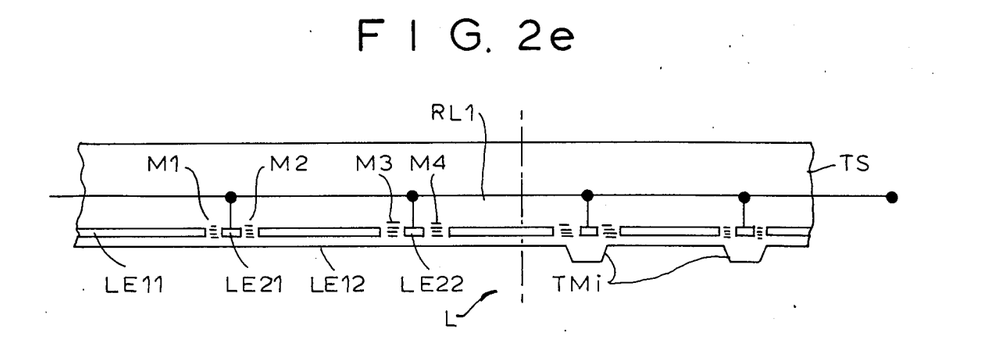

In FIG. 2e, the conductive electrodes $LE1_i$ serve for receiving the potential of the measured solution L, whereas the equalizing conduit RL1 establishes the connection between the electrodes LE21 and a metal electrode of a potential generator or to a reference electrode. In this embodiment, potential-measuring structure $M_i$ are the interspaces between $LE1_i$ and $LE2_i$. In order to avoid errors in reading the measured potentials, the sides of electrodes $LE2_i$ facing the measured solution L have a substantially reduced surface area. These surface areas if desired can be covered by additional insulating layers $IM_i$.

Figure 2F:
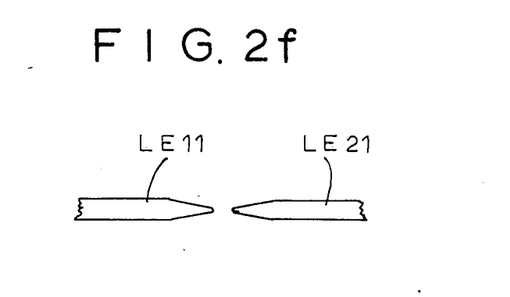

If the conductive electrodes $LE1_i$, $LE2_i$ are produced by etching of metal sheets, it is of advantage when the facing edges of these electrodes are formed in a shape illustrated in FIG. 2f. Due to the sharp edges of these electrodes, a particularly high strength of field in the potential-measuring structure is achieved.

Figure 2G:
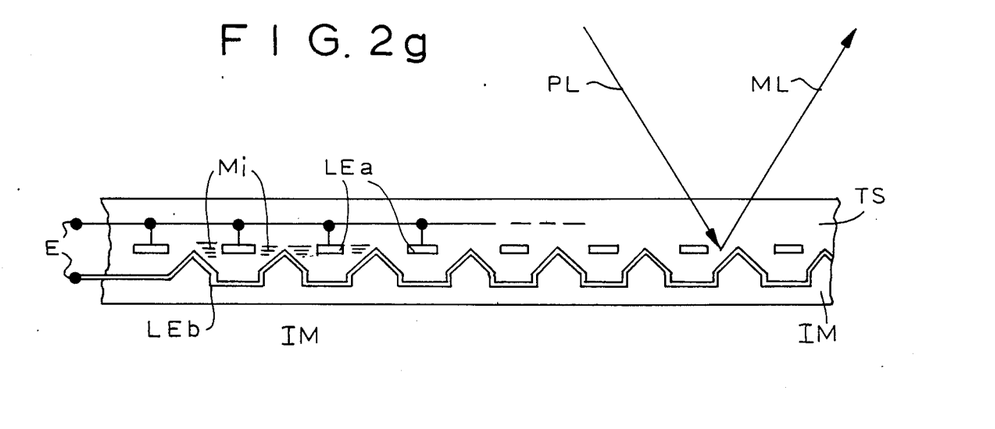
Figure 2H:
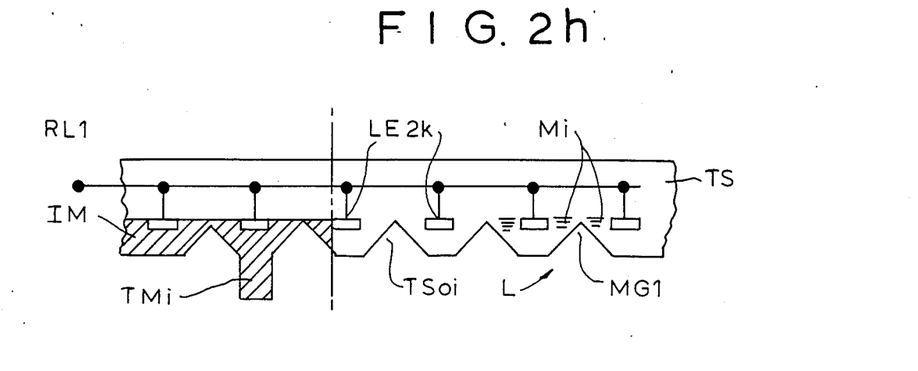

According to FIG. 2h, recesses $TSO_i$ are used instead of conductive electrodes $LE1_i$. These recesses are produced either by embossing the lower surface of the supporting layer TS or by attaching a correspondingly shaped insulating layer IM to the lower surface of the support layer TS. In the first case, the conductive electrode LE2 must be embedded in the supporting layer. In the second case, the electrodes LE2 can be made in a known manner by vapor deposition or by a high-frequency spraying and then covered by an electrically insulating and chemically inert layer applied by a varnishing process or by coating a synthetic material in a vacuum. In this manner the layer IM is applied. The potential-measuring structures $M_i$ are parts of the supporting layer TS or of the insulating layer IM, which are determined by the position of the electrical conductor.

Also in this embodiment of the invention, a mechanically stable device is produced even if the thickness of the potential-measuring structures is kept extremely low.

Figure 2I:
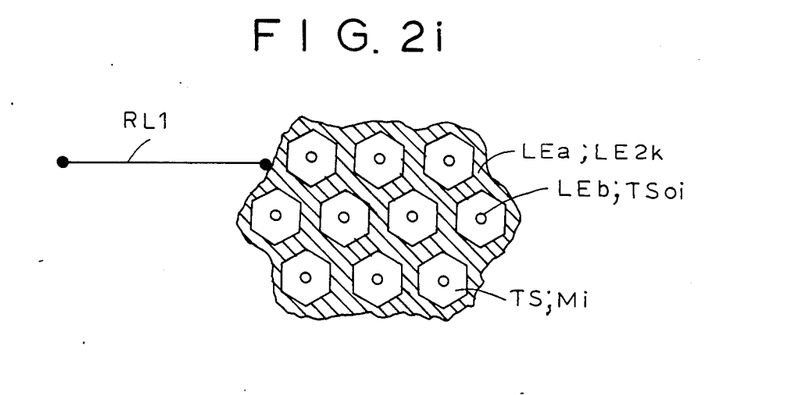
Figure 2K:
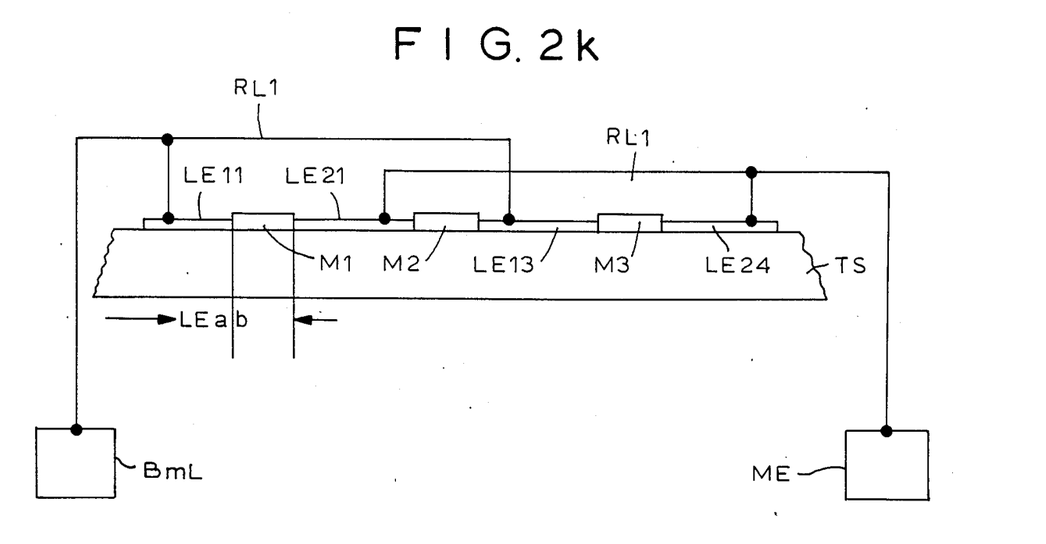

For measuring arbitrary potential differences between metallic conductors, the arrangements according to FIGS. 2g or 2k are used. The arrangement according to FIG. 2g which can be produced by metallizing the side MG1 in the embodiment of FIG. 2h, and by coating the metallized surface by an insulating layer IM, the potential-measuring structures are formed by portion $M_i$ between the conductors $LE_a$, and the metallized layer $LE_b$. The metallized layer $LE_b$ serves simultaneously as a reflector for the measuring light beam ML and the testing light beam PL.

The conductive electrodes $LE_a$, $LE2_k$ according to FIG. 2i are preferably in the form of a sieve with hexagonal meshes. The tips of metallized recesses $LE_b$ or the measured solution L in the conical recesses $TSO_i$ project in the center of the meshes. The entire length of the edges delimits an optical measuring surface. If desired, other forms of the sieve-like arrangement of the electrodes $LE_a$, $LE2_k$ can be used.

FIG. 2k shows in a sectional side view strip-shaped conductive electrodes $LE_{ik}$ arranged on supporting layer TS. In this embodiment, the electric field is created predominantly between the edges of the conductive electrode $LE1_i$ and $LE2_k$ in the potential-measuring structures $M_i$. Also in this case, the field strength due to the minute thickness of the conductive layers $LE_{ik}$ are very high and can be controlled by a suitable selection of spacings between electrodes $LE_{ab}$. The advantage of this embodiment is an improved mechanical hold of the electrodes and potential-measuring structures of the supporting layer and its unsensitivity to mechanical stresses.

The arrangements according to FIGS. 2g and 2k are suitable also for measuring potential differences in arbitrary conductors apart from the second-class conductors.

Figure 2M:
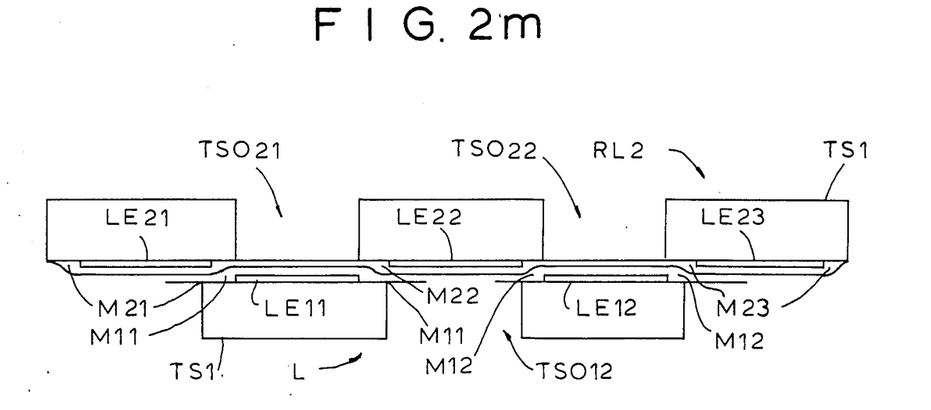

When this invention is to be used exclusively for the second-class conductors, it is advantageous to use two supporting layers TS1, TS2 according to FIG. 2m. The potential difference to be measured is produced across each of two potential-measuring structures $M1_i$, $M2_i$ or $M1_i$, $M2_k$. The second-class conductor fills up the recesses $TSO_{ik}$, and the potential is produced by the effect of conductive electrodes $LE_{ik}$.

If high potential differences such as up to several kilovolts are to be measured, potential-measuring structures of increased thickness are used. The thickness of the structures is adjusted so as to prevent disruptive discharges, and at the same time to preserve a maximum possible field strength for the employed indicators.

Figure 3:
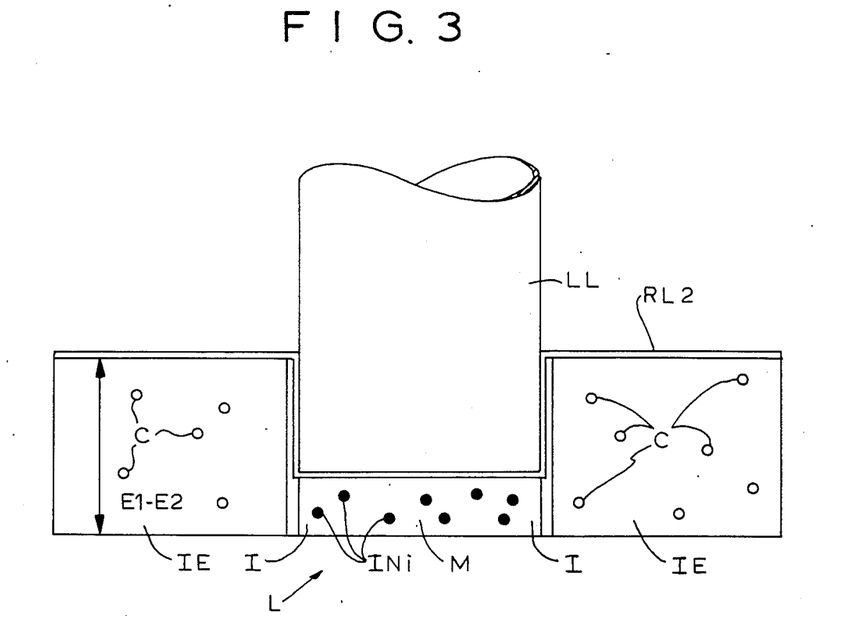
FIG. 3 shows an embodiment of the arrangement of this invention using light conduits.

The arrangement of FIG. 3, which is analogous to that of FIG. 1b, employs an ion-selective membrane IE and a potential-measuring structure M arranged in close proximity one to the other and separated by insulators I. The structures IE and M are interconnected by a common equalizing conductor RL2, so that the potential difference $E1-E2$ generated by the ion-selective transport molecules (carriers) C is immediately applied across the potential-measuring structure M. The indicator molecules $IN_i$ embedded in the potential-measuring structure M, and being of the same type of indicator or a mixture of different indicator types having different characteristic frequencies, produce in response to the applied potential difference a fluorescence which is transmitted via a light conduit LL to a non-illustrated light-measuring device.

Figure 4:
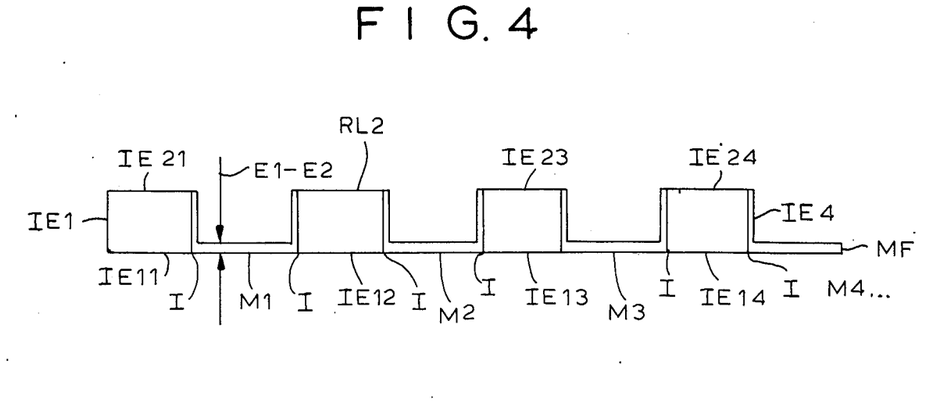
FIG. 4 shows the embodiment employing a measuring mosaic.

FIG. 4 shows a mosaic MF of potential-measuring structures $M_i$ arranged side-by-side and separated by insulators I and of potential generators $IE_k$ defining boundary surfaces $IE_{ik}$. By virtue of this mosaic, the effective potential-measuring surface is increased, and the signal-to-noise ratio of the entire arrangement is improved. The elements of the mosaic can be arranged in different patterns so as to meet all requirements when measuring potential differences in different measuring solutions.

Figure 5A:
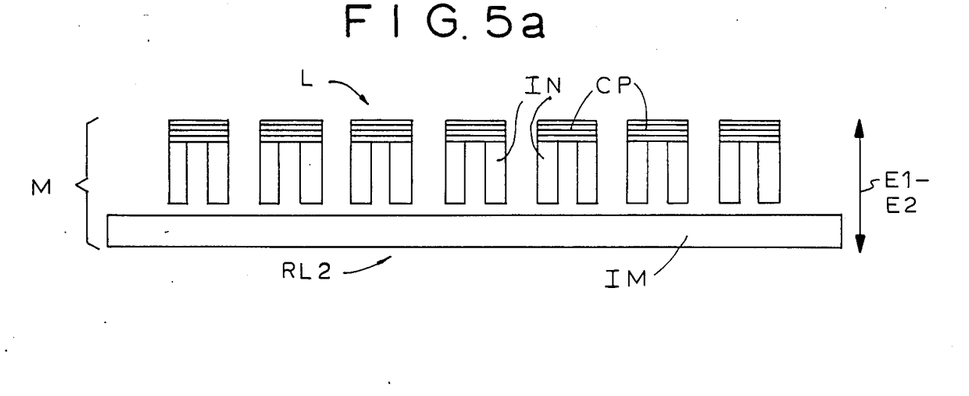
FIGS. 5a and 5b illustrate the construction of laminated potential-measuring structures.

FIG. 5a shows a differential measuring structure M consisting of an extremely thin layer (monolayer) of molecules of an indicator IN interconnected with molecules of a chromophor CP on a layer IM. The indicator molecules IN are in polarized form. Since such layers have a hydrophobic quality, they can be made very thin without undergoing any chemical change in an aqueous solution L, and accordingly a very high field strength and a strong optical signal are obtainable.

Monomolecular layers of this kind form themselves in the interface of two different second-class conductors.

Figure 5B:
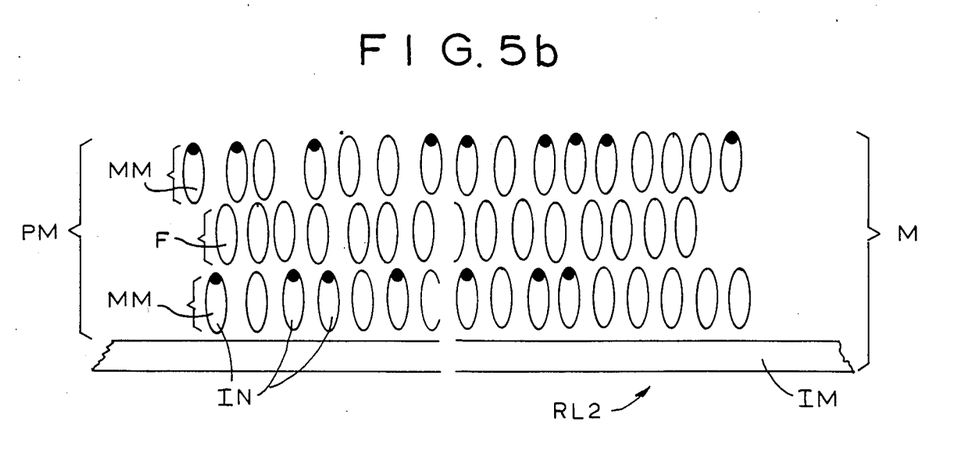

In using conventional preparation methods it is also possible to produce layers PM consisting of several molecular layers and having a definite thickness as illustrated in FIG. 5b. In this example, the monomolecular layers MM are doped with indicators IN and are separated by an interposed indicator-free layer F.

The layers can be also arranged in such a manner that the reaction time to potential changes in the measured solution is very short, and in this case the test light can be modulated to provide for a more effective processing of electrical signals, such as amplification of alternating-current signals, lock-in rectification, reduction of bandwidth, and the like.

Using sensitive indicators, it is possible to measure potential pulses and to use pulsating testing light either in the form of single pulses or a series of pulses. For this mode of operation laser light is of particular advantage because of reduced load of the indicators. The change of optical quality of the indicator follows substantially the pulse-shaped potential change. The waveform of the potential pulse can be utilized for differentiating between signal and noise voltages.

To optimize the time behavior of the arrangements according to this invention, the surface areas of interfaces of the potential-measuring structure, and also the surface areas of the conductive electrodes delimiting the potential-measuring structure, are adjusted to the thickness of the potential-measuring structure. Namely, if the course of a potential pulse is to be determined, the RC time constant and hence the capacity of the entire arrangement is of importance. This capacity can be adjusted by selecting substances of suitable dielectric constant for the potential-measuring structure; the capacity can also be adjusted by different series-parallel connections of several smaller potential-measuring structures and thus the time behavior of the pulse is controlled.

In addition, the electric resistance of conductors or of the second-class conductors can be also utilized for adjusting the RC time constant.

Figure 6A:
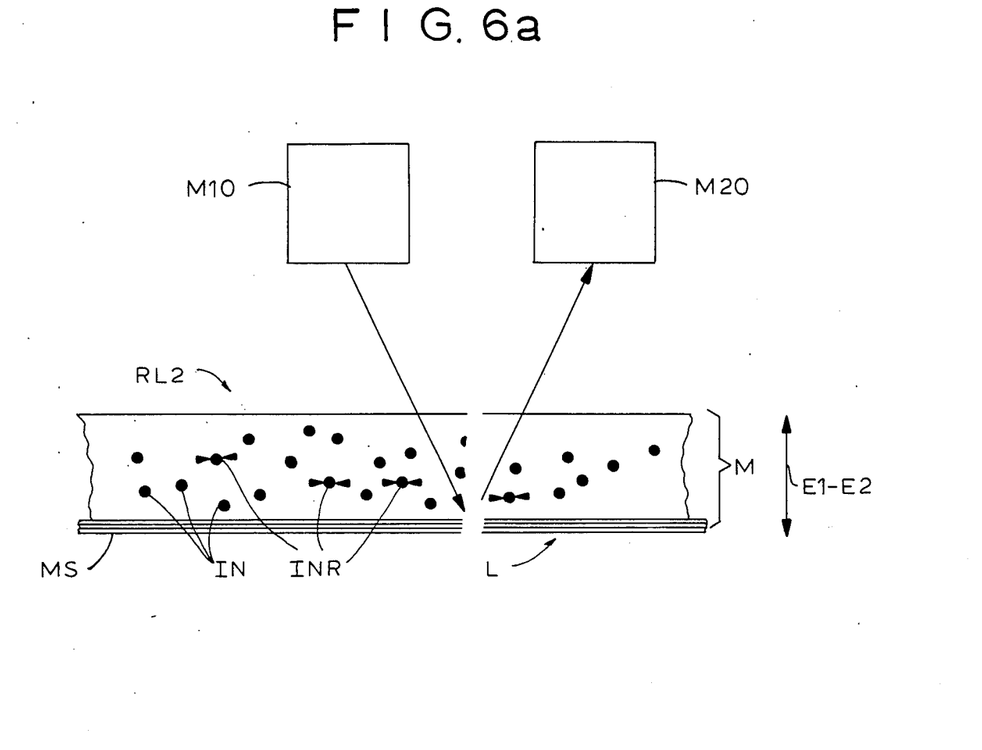
FIGS. 6a and 6b shows the application of auxiliary electrodes and layers for optical decoupling.

According to FIG. 6a, the potential-measuring structure M includes, at the side thereof which is in contact with the measured solution L, a layer MS1 whose optical quality is such as to decouple optically the measuring structure M from the measured solution L. This decoupling is necessary for avoiding optical retroaction from the solution L. The decoupling layer MS1 has a light-reflecting, -refracting, -dissipating or -absorbing quality. The changes in phase, or polarization, luminescence and energy transfer factor for the incoming light beam may also cause the change in the optical quality of the layer.

A lateral transmission of the test light has the advantage that its interaction with the measured solution is reduced in advance. This interaction is further reduced by transmitting the light beam below a critical angle for the total reflection.

Figure 6B:
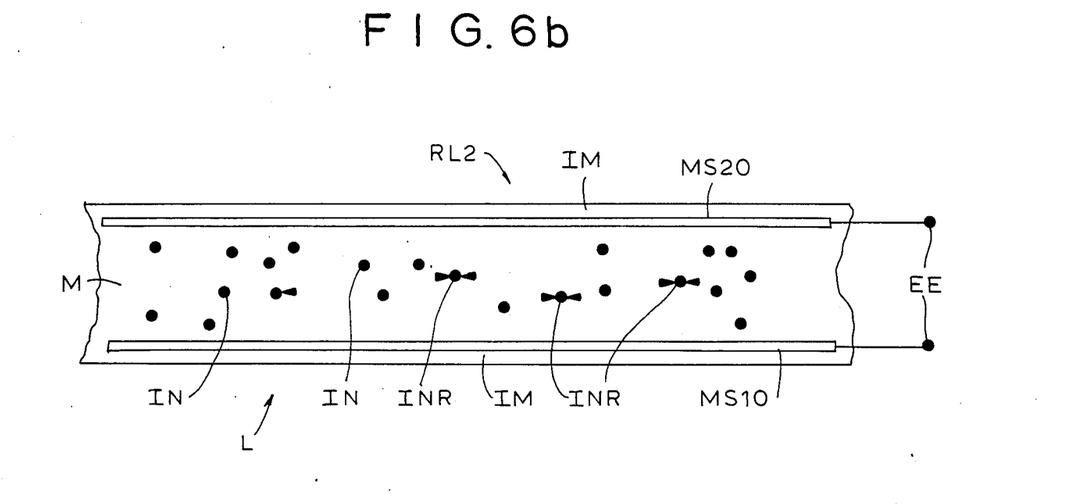

In the embodiment according to FIG. 6b, there are provided layers MS20 and MS10 which are surrounded by an insulating membrane IN. By means of these conductive layers, a biasing voltage can be applied to the potential-measuring structures M, such as a calibration voltage EE by means of which a calibration in situ can be made on the structure. The calibration voltages are applied periodically, and the corresponding calibration signal is used for producing a difference signal or a ratio with the measuring signal.

The upper layer MS20 facing the light-measuring device must be optically transparent. If it is desired to measure by means of this arrangement the potential differences in a measured solution L which does not exhibit any optical retroaction on the testing or measuring light beams, when the latter are used in a direct transillumination method (FIG. 2b), then the opposite layer MS10 must also be optically transparent.

The layers MS10 and IN facing the measured solution L can be also structured in the aforedescribed known manner to serve for an optical decoupling.

In addition, a reference indicator INR whose optical quality is invariable and does not change with the potential difference is provided in the measuring structure M. The reference indicator makes it possible to eliminate in a known manner optical changes such as clouding in the optical path, or failing of the indicators, and also to eliminate electrical changes caused for example by variation in sensitivity of the sensors or by amplification changes.

Figure 7:
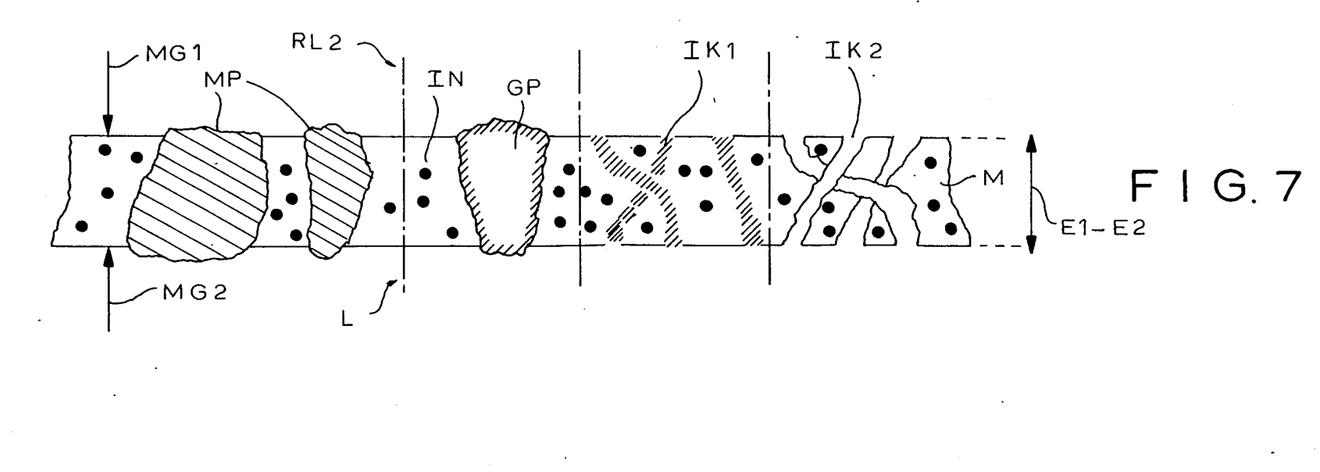
FIG. 7 is a combination of potential generators and potential-measuring structures.

The potential-measuring structure and the potential generator can be integrated in a device illustrated in FIG. 7. In this embodiment, a potential-measuring structure M of a highly insulating material encloses micropotential generators MP, GP, $IK_1$, $IK_2$. Such micropotential generators are created as ion channels, for example in the form of mechanical pores IK2, or regions doped by transport molecules (carrier doping) IK1, or in the form of metal particles MP, or ion-selective glass GP. Across the boundary surfaces or interfaces MG1 and MG2, potential difference $E1-E2$ is produced and optically indicated by indicators IN.

Since the potential-measuring structure M itself is chemically inert and electrically highly insulating, no parasitic potential takes place. The produced potential difference is generated exclusively by the micropotential generators.

Figure 8:
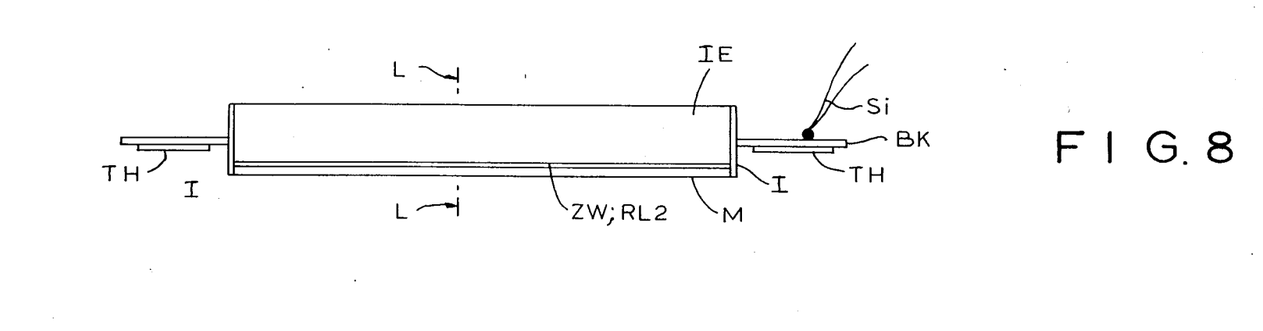
FIG. 8 is a sandwiched construction of a potential generator and a potential-measuring structure.

Another embodiment of a combined arrangement is shown in FIG. 8. In this example, the potential-measuring structure M is connected to the potential generator IE by an equalizing conduit RL2 which is in the form of an intermediate layer ZW. The end walls of the measuring structures are provided with insulators I connected to a construction piece BK which supports means TH for thermal stabilization, such as electrical heating means and thermal sensors Si arranged opposite the thermal stabilizing means. If desired, this arrangement can be combined with other kinds of physical sensors and/or with different arrangements of potential-measuring structures.

It will be understood that each of the elements described above, or two or more together, may also find a useful application in other types of constructions differing from the types described above. For example, the above described constructions can be used in connection with fermentation or oxygenation devices and can be also connected in measuring paths of a process-regulating system.

While the invention has been illustrated and described as embodied in specific examples of the arrangement for measuring potential differences in second-class conductors, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An arrangement for measuring potential differences in second-class conductors, comprising a potential generating body of a meterial which generates an electric potential on its interface with a second-class conductor; a potential measuring body of an electrically insulating and chemically inert material including optical indicators whose optical properties change in response to an applied electrical potential, said potential measuring body defining two opposite surfaces; said potential generating body and one of the two surfaces of said potential measuring body interfacing a measured second-class conductor; electrically conducting means for connecting the other surface of said potential measuring body with a potential generated on the interface of said potential generating body with the second-class conductor; and a light measuring device optically coupled to said optical indicators in said potential measuring body to measure a change of optical properties of said indicators and hence the electric potential applied to said other surface.

2. An arrangement as defined in claim 1, wherein the potential-measuring body is in the form of a thin film.

3. An arrangement as defined in claim 2, wherein the potential-measuring body is in the form of a monomolecular layer.

4. An arrangement as defined in claim 3, wherein said potential-measuring body includes several monomolecular layers superposed one on the other.

5. An arrangement as defined in claim 4, wherein at least one of said monomolecular layers is doped with indicator molecules.

6. An arrangement as defined in claim 4, wherein one of said layers is completely made of indicator molecules.

7. An arrangement as defined in claim 6, wherein the remaining monomolecular layers are free of indicator molecules.

8. An arrangement as defined in claim 5, wherein the indicator molecules are polarized in a preferred direction.

9. An arrangement as defined in claim 1, wherein the potential-measuring body is in the form of a phospholipid membrane.

10. An arrangement as defined in claim 1 wherein the optical indicators in said potential-measuring body are arranged in a flat pattern.

11. An arrangement as defined in claim 1, wherein said potential-measuring body includes a combination of different kinds of optical indicators.

12. An arrangement as defined in claim 1, wherein the potential-generating body and the potential-measuring body are arranged in close spatial proximity relative to each other.

13. An arrangement as defined in claim 12, wherein said potential-generating body and said potential-measuring body are arranged around a common center axis, and the indicators in said potential-measuring body are optically coupled to a light conduit.

14. An arrangement as defined in claim 12, wherein said potential-generating body, said potential-measuring body and said conducting means is an intermediate layer sandwiched between the remaining layers 15. An arrangement as defined in claim 1, wherein a plurality of potential-generating bodies and of potential-measuring bodies are arranged in a mosaic-like surface.

16. An arrangement as defined in claim 1, wherein said potential-measuring body includes means for modifying electric field.

17. An arrangement as defined in claim 16, wherein said field-modifying means include conductive electrodes arranged side-by-side, and said optical indicators being arranged between the opposite edges of the electrodes.

18. An arrangement as defined in claim 17, wherein said potential-measuring body is formed with recesses defining edges or tip points, said second-class conductor filling up said recesses and said optical indicators being provided in the proximity of said edges or points.

19. An arrangement as defined in claim 17, wherein the opposite edges of said conductive electrodes are reduced in thickness to form sharp edges.

20. An arrangement as defined in claim 18, wherein the edges of said electrodes and the edges or points of said recesses are arranged opposite each other to form potential-measuring spaces therebetween.

21. An arrangement as defined in claim 20, said potential measuring body further comprising a supporting layer in which said recesses are formed, said conductive electrodes being arranged in one plane in said supporting layer and alternating with the edges of said recesses.

22. An arrangement as defined in claim 21, wherein said supporting layer is made of a transparent electrically insulating body doped with optical indicating means so as to form a single-piece potential-measuring structure.

23. An arrangement as defined in claim 22, wherein the recesses in said supporting layer have the shape of hexagonal pyramids, and said conducting means is in the form of a planar sieve having hexagonal meshes coinciding with the edges of said pyramids.

24. An arrangement as defined in claim 21, comprising two superposed supporting layers each including a succession of conductive electrodes, the edges of conductive electrodes in one supporting layer being arranged opposite corresponding edges of conductive electrodes in the other supporting layer so as to form potential-measuring spaces therebetween.

25. An arrangement as defined in claim 1, wherein the measured second-class conductor is optically decoupled from the potential-measuring body by absorption, reflection or dispersion of the light from said light-measuring device.

26. An arrangement as defined in claim 1, wherein said potential-measuring body includes an electrically conductive, light-transparent layer for applying an auxiliary electrical potential to said optical indicators.

27. An arrangement as defined in claim 25, wherein said potential-measuring body includes a layer for optically decoupling the optical indicators from the measured second-class conductor.

28. An arrangement as defined in claim 1, wherein said potential generating body is of metal.

29. An arrangement as defined in claim 1, wherein said potential generating body is of ion-selective glass.

30. An arrangement as defined in claim 1, wherein said potential generating body is an ion-selective membrane.

31. An arrangement as defined in claim 28, wherein said conducting means is of metal.

32. An arrangement as defined in claim 1, wherein the conducting means is a second-class conductor.

33. An arrangement as defined in claim 1, wherein said optical indicators are luminescent or fluorescent indicators.

34. An arrangement as defined in claim 33, wherein said optical indicators are of merocyanine.

35. An arrangement as defined in claim 33, wherein the optical indicators are of a styryl dye.

36. An arrangement as defined in claim 33, wherein said optical indicators are of 3,3'-dipropylthiadicarbocyanine-iodide.

37. An arrangement as defined in claim 1, wherein said potential-measuring body includes an optical reference indicator.

38. An arrangement as defined in claim 1, wherein said optical indicators are sealingly embedded in said potential-measuring body.

39. An arrangement as defined in claim 38, wherein the material of said potential-measuring body has a low permeability for acids.

40. An arrangement as defined in claim 38, wherein said optical indicators includes indicator molecules in a covalent bond with the material of the potential-measuring body.

41. An arrangement as defined in claim 38, wherein said optical indicators are enclosed in a membrane.

42. An arrangement as defined in claim 1, wherein said potential-measuring body is an electrically highly insulating membrane, and said potential generating body includes a number of micropotential generators arranged in said membrane.

43. An arrangement as defined in claim 42, wherein said micropotential generators are in the form of mechanical pores.

44. An arrangement as defined in claim 42, wherein said micropotential generators are formed by carrier-doped regions in the potential-measuring structure.

45. An arrangement as defined in claim 42, wherein the micropotential generators are metal particles provided in said potential-measuring body.

46. An arrangement as defined in claim 42, wherein the micropotential generators are particles of ion-selective glass provided in said potential-measuring structure.

47. An arrangement as defined in claim 1, wherein said light-measuring device includes a source of testing light and means for modulating said testing light.

48. An arrangement as defined in claim 1, comprising means for applying the measured potential or the light from said light-measuring device in pulses.

49. An arrangement as defined in claim 48, wherein the surface areas of the two surfaces of the potential-measuring body are adjusted to the thickness of said body such that RC-time constant of the potential-measuring structure is smaller than the duration of said pulses.

50. An arrangement as defined in claim 49, wherein the dielectric constant of the material of said potential-measuring body is so selected such that the RC-time constant of the potential-measuring body is smaller than the duration of said pulse.

51. An arrangement as defined in claim 26, wherein a calibration potential is periodically applied to said auxiliary electrode and an optical signal resulting from said calibration potential is employed as a reference signal.

52. An arrangement as defined in claim 1, wherein said light-measuring device includes a source of light for transmitting a test light beam through a surface of said potential-measuring body, and a light-sensing device arranged for receiving a light from said optical indicator.

53. An arrangement as defined in claim 1, wherein said light-measuring device includes a light source and a light-sensing device arranged at opposite sides of said potential-measuring body.

54. An arrangement as defined in claim 1, wherein said potential-measuring body includes a supporting layer of a light-conductive material and said light-measuring device is arranged at lateral sides of said supporting layer.

55. An arrangement as defined in claim 54, wherein said light-measuring device produces an electrical output signal applicable in radiating systems.

56. An arrangement as defined in claim 1, further comprising sensors attached to said potential-measuring body for sensing additional physical or biological parameters of said second-class conductor.

57. An arrangement as defined in claim 56, further comprising means for thermal stabilization of said sensors and of said potential-measuring body.

58. An arrangement as defined in claim 56, wherein said sensors and said potential-measuring body are arranged on a common construction member.

59. An arrangement as defined in claim 1, wherein said light-measuring device includes a laser beam light source.

60. An arrangement as defined in claim 1, wherein said light-measuring device includes a light source in the form of light-emitting diodes.

61. An arrangement as defined in claim 1, wherein said light-measuring device includes a light sensor in the form of an array of photocells arranged for receiving the light from said indicating means.

62. An arrangement as defined in claim 1, wherein said light-measuring device includes a light sensor in the form of a vidicon.

63. An arrangement as defined in claim 1, wherein said optical indicators in said potential measuring body form a spatial pattern.

* * * * *